United States Patent
Räber et al.

(10) Patent No.: US 9,977,022 B2
(45) Date of Patent: May 22, 2018

(54) METHOD FOR THE DETECTION AND CLASSIFICATION OF PRRSV-INFECTIONS IN SWINE HERDS AND DIAGNOSTIC ANTIGEN COMPOSITIONS FOR SUCH METHODS

(71) Applicant: PRIONICS AG, Carlsbad, CA (US)

(72) Inventors: Alex Räber, Dietikon (CH); Franziska Baader Kuhn, Unterengstringen (CH); Bjorn Schröder, Erlinsbach (CH); Maria Frias Blanco, Majadahonda (ES)

(73) Assignee: PRIONICS AG, Schlieren (CH)

( * ) Notice: Subject to any disclaimer, the term of this patent is extended or adjusted under 35 U.S.C. 154(b) by 0 days. days.

(21) Appl. No.: 14/890,643

(22) PCT Filed: May 14, 2014

(86) PCT No.: PCT/EP2014/001301
§ 371 (c)(1),
(2) Date: Nov. 12, 2015

(87) PCT Pub. No.: WO2014/183870
PCT Pub. Date: Nov. 20, 2014

(65) Prior Publication Data
US 2016/0116471 A1    Apr. 28, 2016

(30) Foreign Application Priority Data
May 15, 2013  (EP) .................................... 13002540

(51) Int. Cl.
*G01N 33/569* (2006.01)
(52) U.S. Cl.
CPC ... *G01N 33/56983* (2013.01); *G01N 2333/08* (2013.01); *G01N 2469/20* (2013.01)
(58) Field of Classification Search
None
See application file for complete search history.

(56) References Cited

U.S. PATENT DOCUMENTS

2004/0014028 A1    1/2004 Lopez et al.

FOREIGN PATENT DOCUMENTS

| WO | WO 96/06619 | * | 7/1996 |
| WO | WO 96/40932 | * | 12/1996 |
| WO | WO 98/50426 | * | 5/1998 |
| WO | 1998050426 | | 11/1998 |
| WO | 2010062395 | | 6/2010 |
| WO | WO 2011/045056 | * | 4/2011 |

OTHER PUBLICATIONS

Balasuriya et al. (Veterinary Immunology and Immunopathology. 204; 102: 107-129).*
Mateu and Diaz (The Veterinary Journal. 2008; 177; 345-351).*
Wang et al. (Virus Research. 2013; 171: 150-160).*
The sequence alignment of instant SEQ ID No. 2 with geneseq database access No. AAW84318 by Van Nieustadt et al in WO9850426 on Nov. 1998.*
Sequence alignment of instant SEQ ID No. 4 with Geneseq database accession No. AAW84324 on Nov. 1998 in WO9850426 by Van Nieuwstadt et al.*
Sequence alignment of instant SEQ ID No. 7 with geneseq database access No. AAW84252 by Van Nieustadt et al in WO9850426 on Nov. 1998.*
Sequence alignment of instant SEQ ID No. 10 with geneseq database access No. AAW84324 by Van Nieustadt et al in WO9850426 on Nov. 1998.*
Sequence alignment of instant SEQ ID No. 5 with Geneseq database access No. AAE94723 by Paul et al. In WO9606619 on Mar. 1996.*
Sequence alignment of instant SEQ ID No. 6 with Geneseq database access No. AZH31389 by Ulbert et al in WO2011045056 on Apr. 2011.*
Sequence alignment of SEQ ID No. 8 with geneseq database access No. AAW25975 by Paul et al. on Dec. 1996 in WO9640932.*
Sequence alignment of SEQ ID No. 9 with geneseq database access No. AAW25967 by Paul et al. on Dec. 1996 in WO9640932.*
EP13002540 European Search Report dated Jul. 12, 2013, 2 Pages.
PCT/EP2014/001301 International Search Report and Written Opinion dated Sep. 3, 2014, 6 pages.
Plagemann, P. "GP5 ectodomain epitope of porcine reproductive and respiratory syndrome virus, strain Lelystad virus", *Virus Research*, vol. 102 (2), 2004, pp. 225-230.
Plagemann, P. "Neutralizing Antibody Formation in Swine Infected with Seven Strains of Porcine Reproductive and Respiratory Syndrome Virus as Measured by Indirect ELISA with Peptides Containing the GP5 Neutralization Epitope", *Viral Immunology*, vol. 19 (2) 2006, pp. 285-293.
Vanhee, M. "Characterization of antigenic regions in the porcine reproductive and respiratory syndrome virus by the use of peptide-specific serum antibodies" *Vaccine, Elsevier Ltd.*, GB, vol. 29 (29), 2011, pp. 4794-4804.

* cited by examiner

*Primary Examiner* — Shanon A. Foley

(57) ABSTRACT

Method for the detection and classification of PRRSV-infections in swine herds, comprising a) the incubation of tissue samples taken from the animals with at least one antigen capable to bind a neutralizing antibody against the Type I-virus possibly present in the animal and with at least one antigen capable to bind a neutralizing antibody against the Type II-virus possibly present in the animal, b) testing whether a binding of antibodies against the Type I-virus and/or the Type II-virus has taken place and c) determining from the presence of possible epitope-antibody complexes whether an infection of the PRRSV I-Type and/or PRRSV II-Type is present in the herd and diagnostic compositions for such a method.

7 Claims, 3 Drawing Sheets

METHOD FOR THE DETECTION AND CLASSIFICATION OF PRRSV-INFECTIONS IN SWINE HERDS AND DIAGNOSTIC ANTIGEN COMPOSITIONS FOR SUCH METHODS

The invention relates to a method according to claim 1 and diagnostic compositions according to claim 9.

Porcine reproductive and respiratory syndrome (PRRS) is one of the most devastating viral diseases causing significant economic losses to the swine industry. The agent responsible for this endemic disease is the PRRS virus (PRRSV) which is easily transmitted via infected pigs through urine, semen and fomites, infecting almost exclusively pig monocytes and macrophages.

Porcine reproductive and respiratory syndrome (PRRS) emerged first in the United States of America in 1987 and subsequently spread worldwide. The syndrome is characterized mainly by reproductive failure in pregnant sows, high mortality in piglets and respiratory problems such as dyspnoea. The cause of these symptoms is an enveloped positive single-stranded RNA virus. The PRRSV belongs to the Arteriviridae family and it infects almost exclusively swine monocytes and macrophages.

The genome is approximately 15 kb and has an UTR region on 5' followed by nine open reading frames (ORF): ORF1a, ORF1b, ORFs2a and 2b, 3 to 7. ORF1a and ORF1b constitute about 75% of the virus genome encoding for proteins with replicase and polymerase activities, whereas ORF 2 to 5 appear to encode for membrane-associated proteins or glycoproteins (GP). ORF6 encodes for a viral unglycosylated membrane protein M and ORF7 encodes for a highly conserved basic protein, N, that constitutes the nucleocapsid. Mutations take place predominantly in the nsp2 region of ORF 1a and the envelope proteins GP3, GP4 and GP5.

Both Type I and Type II strains have a number of neutralizing and immunodominant epitopes.

Sensitivity to antibody-mediated neutralization was tested for a selected number of antigen regions (AR) by in vitro virus-neutralization tests on alveolar macrophages with peptide-purified antibodies. In addition to the known neutralizing epitope in GP4, one in GP3 turned out to be targets for virus neutralizing antibodies. Since the neutralizing AR in GP3 induced antibodies in a majority of infected pigs, the immunogenicity of this AR was studied extensively, and it was demonstrated that the corresponding region in GP3 of virus strains other than Lelystad Virus (PRRSV type 1) also induces virus neutralizing antibodies. This provides new insights into PRRSV antigenicity, and contributes to the knowledge on protective immunity and immune evasion strategies of the virus (vanhee et al; 2011).

Since ARs GP3 and GP4 were both immunogenic and target for neutralizing antibodies, the serum antibody response against these ARs was further studied (vanhee et al; 2011). While antibodies against GP4 appeared relatively fast upon infection in a majority of the animals, it clearly lasted longer for most animals to develop antibodies against AR GP3. Moreover, antibody titers in sera and alveolar fluids against GP3 were invariably lower than against GP4.

Based on the genetic differences of the virus, it is possible to encounter two main types: European genotype (Lelystad virus or Type I) and American genotype (VR-2332 virus or Type II). These PRRSV genotypes have a nucleotide identity between 55% and 70% when both genomes are compared.

Protection against PRRSV infection is not possible and prevention of virus replication is not mediated by the humoral response alone. Cellular immunity is critical to prevent clinical signs of PRRS.

Nowadays, there are mainly two commercially available modified live vaccines (MLV) on the market; one is composed of an EU type (Porcilis® PRRS) and the other one of a US type PRRSV (Ingelvac® PRRS). Both vaccines demonstrate an overall efficiency and are widely used for the prevention of PRRSV induced clinical symptoms.

PRRS MLV vaccine confers effective genotype/strain-specific protection, but provides only partial protection against genetically heterologous PRRSV. Before the emergence of atypical PRRS, it was generally assumed that the reproductive consequences of infection with PRRSV, including abortion, were due to the direct effect of the virus on the conceptus following transplacental infection. While this is certainly true for many cases of PRRSV-induced reproductive failure, it apparently does not explain all cases, because many litters aborted during epidemics of atypical PRRS were found free of infection. The latter observation indicates that abortion can also be the result of a systemic reaction. The additional observation that abortions were common in herds that had previously been vaccinated raised the question of whether an acute—anamnestic immune response contributed to the clinical picture. If so, there is a possibility that exposure to a virulent field strain of PRRSV other than that used in the vaccine elicits a response different than what would have followed exposure of a naive gilt or sow to the same strain. That is not to say vaccination is not beneficial overall, but it is possible that prevalence of one aspect of reproductive failure, namely abortion, may be slightly higher in vaccinated herds than in non-vaccinated herds. (W. L. Mengeling, K. M. Lager, A. C. Vorwald The effect of porcine parvovirus and porcine reproductive and respiratory syndrome virus on porcine reproductive performance. Animal Reproduction Science 60-61_2000. 199-210)

In such cases, sows often lack neutralizing antibodies against one type of PRRSV. This might be why it is imperative to continuously vaccinate herds with one type of PRRS MLV vaccine since it may displace the other PRRSV type in the herd. In case of a field infection with the counter PRRSV strain, these animals may not be properly protected; cross protection of vaccines against PRRSV of the other type is not fully convincingly shown.

WO 2010/062395 discloses an assay which allows the differentiation of serum antibodies against Type I and/or Type II PRRSV utilizing PRRSV nsp7 from both strains as antigen.

In order to improve vaccine and sanitary management in farms it might be of interest to be aware of a more detailed infectious status of a herd, e.g. to distinguish chronic infections or vaccination from fresh infections.

Such information can be crucial in the further treatment of the animals.

The object of the invention is to provide an improved test method for PRSSV and diagnostic compositions for such method.

The object is achieved by a method according to claim 1 and a composition according to claim 9. Embodiments of the invention are addressed to by the subclaims.

According to the invention a method is provided for the detection and classification of PRRSV-infections in swine herds, comprising the incubation of tissue samples taken from the animals with at least one antigen capable to bind a neutralizing antibody against the Type I-virus possibly present in the animal and with at least one antigen capable to bind a neutralizing antibody against the Type II-virus possibly present in the animal. After incubation it is tested, whether a binding of antibodies against the Type I-virus and/or the Type II-virus with the antigens has taken place and it is determined from the presence of possible antigen-antibody complexes whether an infection of the PRRSV I-Type and/or PRRSV II-Type is present in the herd.

The term tissue is used in a broad sense. Apart from its literal meaning it shall also encompass body fluids like blood, plasma, serum or urine.

The antigens used are selected from PRRSV Type I and Type II peptide sequences containing a neutralizing epitope.

Peptides of GP3 Type I (EU) which can be used with the invention include peptides containing a sequence according to SEQ ID NO. 6. Examples for such peptides are apart from a peptide consisting of SEQ ID NO. 6 peptides with sequences according to SEQ IDs NO. 1 and 5.

Peptides of GP3 Type II (US) which can be used with the invention include peptides containing a sequence according to SEQ ID NO. 8. Examples for such peptides are apart from a peptide consisting of SEQ ID NO. 8 peptides with sequences according to SEQ IDs NO. 3 and 9.

Peptides of GP4 Type I (EU) which can be used with the invention include peptides containing a sequence according to SEQ ID NO. 7. A further example for such a peptide apart from a peptide consisting of SEQ ID NO 7 is a peptide with a sequence according to SEQ ID NO. 2.

Peptides of GP4 Type I (US) which can be used with the invention include peptides containing a sequence according to SEQ ID NO. 10. A further example for such a peptide apart from a peptide consisting of SEQ ID NO 10 is a peptide with a sequence according to SEQ ID NO. 4.

A list of the peptides mentioned above is given in the following:

```
Type I (EU) PRRSV

SEQ ID NO: 1 (GP3 LV 30AA54):
ICMPCSTSQA ARGRLEPGRS NMCRKGHDRC

SEQ ID NO: 2 (GP4 LV4)
DINCFRPHGV SAAQEKISFG KSSQCREA VGTP

SEQ ID NO. 5 (GP3):
STSQAARQRL EPGRNMWCKI GHDRCEER

SEQ ID NO. 6 (GP3)::
STSQAARQRL EPGRNMW

SEQ ID NO. 7 (GP4)::
FRPHGVSAAQ EKISFGKSS

Type II (US) PRRSV

SEQ ID NO: 3 (GP3 VR):
VCPPCLTRQA ATEIYEPGRS LWCRIGYDRC EEDHDELGFM

SEQ ID NO: 4 (GP4 VR):
DISCLRHRDS ASEAIRKIPQ CRTAIGTP

SEQ ID NO. 8 (GP3)::
YEPGRSLWCR IGYDRCGEDD

SEQ ID NO. 9 (GP3)::
IYEPGRSLWC RIGYDRCGED DHDEL

SEQ ID NO. 10 (GP4)::
HRDSASEAIR KIPQCRTAI
```

The above mentioned peptides are examples. It is clear for a person skilled in the art that further peptides containing sequences according to SEQ IDs NO. 6, 7, 8 or 10, respectively, can have similar antigenic properties which allow the diagnostic testing of animals and thus are also encompassed by the invention. The length of such peptides is limited by their ability to differentiate between PRRSV Type I and II in diagnostic tests. Such ability should be given for peptides not longer than 50 amino acids including the above mentioned sequences.

GP4 and GP3 protein is very well conserved between genotypes and it can be used as a target for extremely specific serological detection by e.g. indirect Enzyme-Linked Immunosorbent Assay (ELISA), due to its capacity to produce neutralizing antibodies. The above mentioned epitopes have been proven to induce the generation of neutralizing antibodies first by vanhee et al; 2011, but previously described by Oleksiewicz M B, Botner A, Toft P, Grubbe T, Nielsen J, Kamstrup S, et al. Emergence of porcine reproductive and respiratory syndrome virus deletion mutants: correlation with the porcine antibody response to a hypervariable site in the ORF 3 structural glycoprotein. Virology 2000; 267: 135-40. Oleksiewicz M B, Botner A, Toft P, Normann P, Storgaard T. Epitope mapping porcine reproductive and respiratory syndrome virus by phage display: the nsp2 fragment of the replicase polyprotein contains a cluster of B-cell epitopes. J Virol 2001; 75: 3277-90.

Especially preferred is to use the sequences according to SEQ ID NO: 2, 4 7 and 10 of GP4 which as stated above contains a neutralizing and immunodominant epitope in its N-terminal for both Type I and Type II strains. Although most pigs are able to develop antibodies against both ARs, GP4 clearly shows the highest immunogenicity in the context of infection. There is evidence from recent studies that AR GP4 is susceptible to antibody-mediated selective pressure in vivo, and its high variability confirms that aminoacid changes in this region are generally well tolerated by the virus.

When the GP4 sequences of aminoacids of both Type I and Type II strains are compared ([GenBank: AAA46277.1]; [GenBank: ABB18277.1]), it is observed that the neutralizing epitope is situated within the most variable region of the GP4 protein. Since GP4 shows such great variability in both genotypes, it can be used as a very specific target for the detection of the virus in infected pigs.

As further specified below it is possible to e.g. develop indirect ELISA detection method using a peptide containing a neutralizing epitope in order to discriminate Type 1 and Type 2 PRSSV.

In a further preferred embodiment it is provided that to use a cocktail of peptides, e.g. the above mentioned SEQ ID Nos: 1-4. The use of such a cocktail leads at least in some cases to a broader immune response.

As stated above the main feature of the invention is that method uses antigenic sequences which include neutralizing epitopes. By using such antigens it is possible to detect the presence of neutralizing antibodies possibly present in the animals. However, neutralizing antibodies are only present in animals for a certain period post infection or vaccination. In case that PPRSV is permanent present in a given herd situation (boars) or repeated vaccination (in the following such cases will be referred to as repeated infections) it may happen that in infected animals no neutralizing antibodies are detectable.

For such cases it may be preferable if an additional standard assay for PRRSV is performed, which detects antibodies normally directed against non neutralizing epitopes (e.g. GP7). In an infectious or vaccinated situation animals with repeated infection turned positive in such a screening test.

With this embodiment of the method a very detailed classification of the status of possible infections in the herd is possible especially if further information on the herd normally available, like e.g. date of vaccination etc., is taken into account. If e.g. the standard test is positive and the titre of neutralizing antibodies is negative or low this means that there is a chronic infection in the herd. If on the other hand the standard assay is positive and the test for neutralizing antibodies provides a high titre this means that there is a fresh infection in the herd.

Summing up the method according to the invention allows a much more detailed evaluation of the infection status in a herd compared to known assay formats since it considers the humoral immune response against neutralizing epitopes in addition to the information available on the herd. On the basis of such evaluation pork producers can e.g. assess the risk of facing clinical signs of a PRRSV infection despite vaccination and can adapt their vaccination strategy, e.g. consider treating animals with either a commercially available Type I or Type II modified live vaccine. Additionally, the measurement of the neutralizing antibody titre against PRRSV Type I or Type II may also give an indication of the fitness of a herd against potential PRRSV infection if neutralisation AB titre of only one type can be detected but infected with the other one. This is the reason why a high specificity test as described below capable of distinguishing between Type I and Type II in one single run may benefit the PRRSV diagnostic.

The invention is also directed to diagnostic compositions which can be used in the method according to the invention. Such compositions include at least the GP4 sequences indicated above, but can also include further antigenic sequences (GP3). As a rule the sequences are immobilized, e.g. by coating on a plate or coupling to beads. The compositions furthermore include all buffers and controls which normally are present in such compositions. A detailed composition is given in Example 1.

Figure 1:
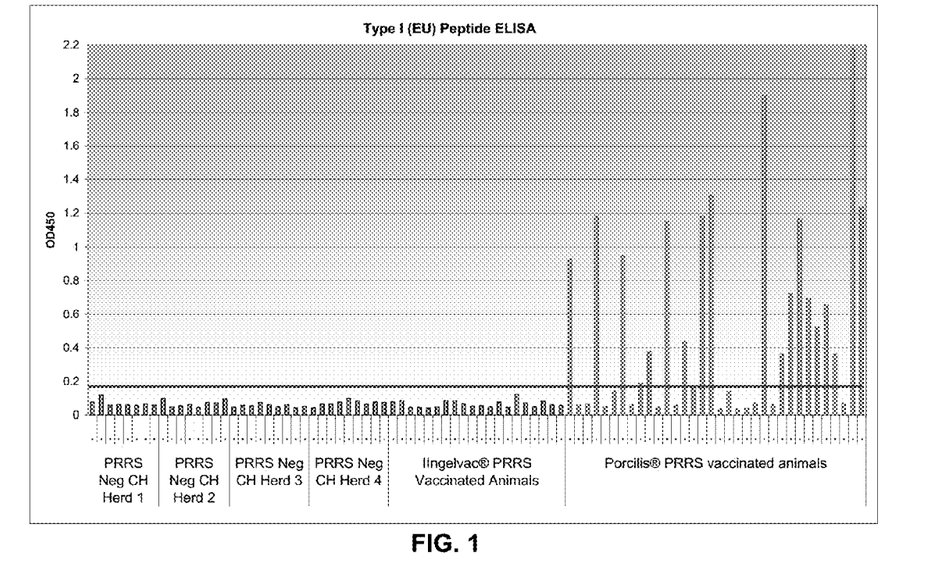
FIG. 1 Illustration of OD 450-620 nm values for different PRRSV sera measured using EU-specific antigen, FIG. 2 Illustration of OD 450-620 nm values for different PRRSV sera measured using US-specific antigen, FIG. 3 Illustration of OD 450-620 nm values for different PRRSV sera measured using a combination of further EU-specific antigenic peptides, FIG. 4 Illustration of OD 450-620 nm values for different PRRSV sera measured using a further combination of EU-specific antigenic peptides, FIG. 5 Illustration of OD 450-620 nm values for different PRRSV sera measured using a combination of further US-specific antigenic peptides, FIG. 6 Illustration of OD 450-620 nm values for different PRRSV sera measured using a further combination of US-specific antigenic peptides.

In the following the invention shall be described further in detail by means of figures and examples:

FIG. 1 illustrates OD 450-620 nm values for PRRS negative (CH Herds 1 to 4) and PRRSV positive sera samples (Porcilis® PRRS and Inlgevac® PRRS vaccinated animals) using a high binding plate coated with 1 µg/ml of GP4_LV4. Stabilcoat had been used for blocking and 0.2% casein in Stabilcoat and PBS 13 1X+0.1% Tween-80 had been used as sample diluent and conjugate buffers, respectively.

Figure 2:
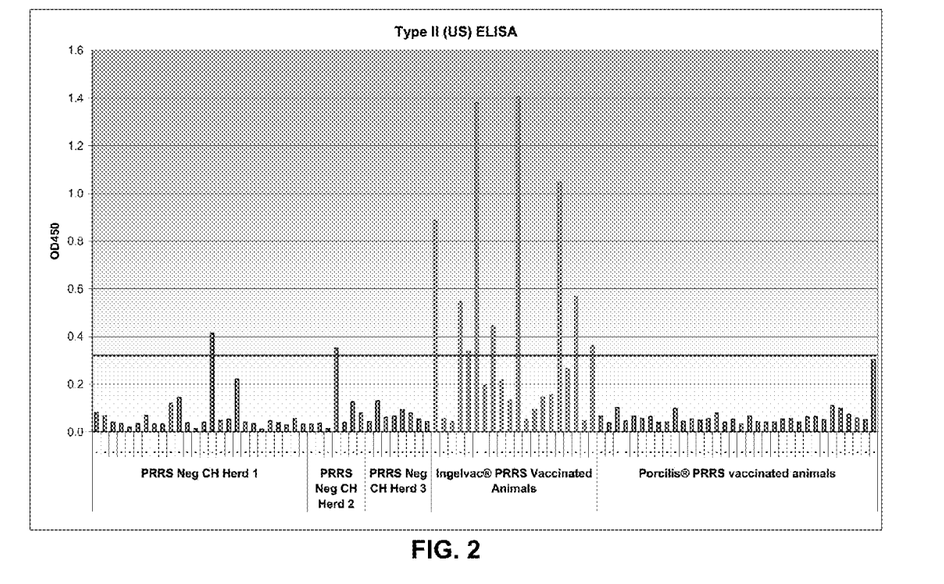

FIG. 2 illustrates OD 450-620 nm values for PRRS negative (CH Herds 1 to 3) and PRRS positive sera samples (Porcilis® PRRS and MLV or Ingelvac® PRRS vaccinated Animals) using a high binding plate coated with 10 µg/ml of GP4_VR_2332_4. Stabilcoat had been used for blocking and 0.2% casein in Stabilcoat and 0.1% Tween-80+0.2% Casein in PBS 13 1x had been used as sample diluent and conjugate buffers, respectively.

FIGS. 3-6 illustrate the results of tests with combinations of further antigenic peptides on different PRRSV sera. For details see example 11.

EXAMPLE 1

Development of an Indirect ELISA a) Antibodies

A secondary antibody was used as conjugate for the detection of neutralizing antibodies (Goat anti Pig IgG (Fc) HRP; stock concentration 1 mg/ml [AbD Serotec, AAI41P]) present in the PRRS samples.

b) Antigen

The antigen used for the development of this indirect ELISA was GP4 peptide from the European PRRSV strain and the American PRRSV strain according to SEQ ID NOs: 1 and 2. The Type I peptide (EU) used shall also be designated as GP4_LV4. The stock concentration of this peptide was 3 mg/ml in $H_2O$. Peptide GP4_VR_2332_4 corresponds to the Type II or US strain and had a stock concentration of 2 mg/ml in $H_2O$. The optimal coating concentration of GP4 LV4 was 1 µg/ml whereas for GP4_VR_2332_4 was 10 µg/ml.

c) Sera Samples

Samples of known status have been used for the development of this indirect ELISA. For Type I PRRSV, a panel of serum samples from 34 pigs that had been previously vaccinated with Porcilis® PRRS. For Type II PRRSV, serial sera samples were obtained from 20 pigs that had been vaccinated with Ingelvac® PRRS MLV. In addition to PRRSV positive samples, 127 PRRSV negative samples from negative control animals were used for validation of the indirect ELISA. These PRRS negative samples were collected from different locations over Switzerland (Bazenheid, Basel, Zürich [ShZh, Zh]) in 2012. All of these samples were also assayed in the Idexx PRRS ELISA.

d) Details of Indirect ELISA (i) Coating of ELISA plates: A high binding plate (Greiner Bio-One 762071-CED) was coated with 100 µl of antigen solution per well. Depending of the antigen used for the coating, the final concentration was 1 µg/ml for GP4_LV or 10 µg/ml for GP4_VR_2332_4. The coating buffer in which the antigen was diluted in was PBS 13 1x with a pH 9.6. The incubation of the antigen took place at 4° C. without shaking overnight.

(ii) Blocking: After antigen incubation overnight, the plate was washed four times with 300 µl of Washing Buffer (0.5% Tween-80 [Sigma P8074-500 ml] in PBS 13 1x) using Tecan Hydroflex washer. Next, 200 µl of Blocking Buffer (StabilCoat Immunoassay Stabilizer [SurModics Prod.Nr. SC01-100]) were added per well. The plate was incubated for 2 hours at room temperature without shaking. After incubation period, the Blocking Buffer was drained and the plate was dried in a 37° C. incubator for 2 hours.

(iii) Dilution of sera samples: Before testing, samples were diluted 1:50. The dilution took place in Sample diluent buffer (0.2% casein in StabilCoat).

(iv) Capture: To each well on the plate, 100 µl of the 1:50 dilution of the serum sample was added. The incubation of the samples took place at room temperature for one hour without shaking. After the incubation period, the plate was washed four times with 300 µl of Washing Buffer (0.05% Tween-80 [Sigma P8074-500 ml] in PBS 13 1x) using Tecan Hydroflex washer.

(v) Detection: After washing the plate, 100 µl of anti Pig IgG (Fc) HRP (20 ng/ml Conjugate Diluent) were added per well. Incubation took place at room temperature for 1 hour without shaking. Next, the plate was washed four times with 300 µl of Washing Buffer (0.05% Tween-80 in PBS 13 1X) using Tecan Hydroflex washer. After washing, 100 µl of TMB substrate (SurModics TTMB-1000-01) were added per well. The plate was then incubated at room temperature for 15 minutes without shaking. For stopping the reaction, 100 µl of Stop buffer solution (0.5M $H_2SO_4$ [Fluka 38294]) were added per well. The absorbance of the coloured reaction was measured using Tecan Sunrise (Measurement wavelength: 450 nm; Reference wavelengths: 620 nm; Read mode: normal).

e) Determining Cut-Off Values

To set negative/positive cut off values, both the mean and the standard deviation of the negative samples only (Bazenheid, Basel, Zurich [ShZh, Zh]) were calculated. Once both values were obtained, the standard deviation was multiplied by a factor of 5; the product of this calculation was added to the negative mean previously calculated.

TABLE 1.

Calculation of Cut-Off values

|  | Mean Negative Samples | Standard Deviation of Negative Samples | Cut-Off (Neg. Mean + Std. Dev*5) |
|---|---|---|---|
| GP4_LV4 | 0.07 | 0.02 | 0.17 |
| GP4_VR_2332_4 | 0.06 | 0.05 | 0.32 | f) Calculation of Sensitivity and Specificity

The sensitivity is calculated to know the probability that a test will give a positive result when the disease is present and it can be calculated using the following formula and following the scheme above (TABLE 5):

Sensitivity=$(A/A+C)*100$

On the other hand, the specificity of an assay will provide information about the probability that a test will give a negative result when the disease is not present. It can be calculated using the formula below and following the scheme above (TABLE 2):

Specificity=$(D/B+D)*100$

TABLE 2

Scheme for calculating sensitivity and specificity

|  |  | Sample Status | | |
|---|---|---|---|---|
|  |  | Positive | Negative | |
| Test | Positive | A | B | A + B |
|  | Negative | C | D | C + D |
|  |  | A + C | B + D | Total | g) Results

As indicated above animals that were vaccinated with EU or US type as well as PRRSV negative animals were tested in order to calculate the specificity and sensitivity of the assay (TABLES 3 and 4 and FIGS. 1 and 2) to determine the specificity and sensitivity of the indirect ELISA, a cut-off of 0.17 and 0.32 at herd level was calculated for GP4_LV4 and GP4_VR_2332_4, respectively. With the gathering of all the data, we determined that the specificity and sensitivity of GP4_LV4 was 99.41% and 55.80%, respectively, whereas for GP4_VR_2332_4, the specificity was 98.91% and the sensitivity 45%. For the calculation of the diagnostic specificity, the PRRS positive samples that were negative depending on the GP4 peptide used were considered as negative.

For the ELISA, although the sensitivity is important, it is of higher interest that the assay is specific, since the main objective of this detection method is to be able to correctly classify individuals as disease-free and avoid false positives.

TABLE 3

Results of optimum ELISA conditions for GP4_LV4 (PRRSV Type I)

|  | TEST GP4_LV4 (EU) | | |
|---|---|---|---|
|  | Total | Positive | Negative |
| Type 1-Sera | 34 | 19 | 15 |
| Type 2-Sera | 20 | 0* | 20 |
| Negative PRRSV antibody serum samples | 152 | 1** | 151 |

As one can take from TABLE 3, no cross detection between EU and US could be observed and only one false positive sample was observed by testing PRRSV negative antibody serum.

TABLE 4

Results of optimum ELISA conditions for GP4_VR_2332_ (PRRSV Type II)

|  | TEST GP4_VR_2332_4 (US) | | |
|---|---|---|---|
|  | Total | Positive | Negative |
| Type 1-Sera | 34 | 0* | 34 |
| Type 2-Sera | 20 | 9 | 11 |
| Negative PRRSV antibody serum samples | 151 | 2** | 149 |

TABLE 4 shows no cross detection between EU and US and only two false positive were observed by testing PRRSV negative serum.

EXAMPLES 2-8 and 11

Examples 2-8 show the results of ELISA analysing blinded samples derived from different pig herds or sera with known status (example 11). The herein described ELISA can also be used for the assessment about the immunological status of a herd related to the presence or absence of neutralization antibodies directed against special epitopes of GP3 and GP4. Further on statements about a fresh or continuous infection situation in a given herd situation can be drawn by consideration the titer level in animals.

Result interpretation for examples 2-8 need additional information alongside the discriminating ELISA e.g. information about the single animal, herd status, and the result of a screening ELISA is needed.

For examples 2-8 and 11 the experiments were done in the identical manner as described for Example 1 with the exceptions that the antigens represented combinations of GP3 and GP4 peptides. The used peptide sequences in examples 2-8 are indicated in the following:

Peptides used:

```
Type I (EU) PRRSV

GP3 LV 30AA54 (SEQ ID NO. 1):
ICMPCSTSQA ARGRLEPGRS NMCRKGHDRC

GP4 LV4 (SEQ ID NO. 2):
DINCFRPHGV SAAQEKISFG KSSQCREA VGTP

Type II (US)

GP3 VR (SEQ ID NO. 3):
VCPPCLTRQA ATEIYEPGRS LWCRIGYDRC EEDHDELGFM

GP4 VR (SEQ ID NO. 4):
DISCLRHRDS ASEAIRKIPQ CRTAIGTP
```

The additional peptide sequences used in example 11 are indicated in the following:

```
Type I (EU) PRRSV

GP3 (SEQ ID NO. 5):
STSQAARQRL EPGRNMWCKI GHDRCEER

GP3 (SEQ ID NO. 6):
STSQAARQRL EPGRNMW

GP4 (SEQ ID NO. 7):
FRPHGVSAAQ EKISFGKSS

Type II (US)

GP3 (SEQ ID NO. 8):
YEPGRSLWCR IGYDRCGEDD

GP3 (SEQ ID NO. 9):
IYEPGRSLWC RIGYDRCGED DHDEL

GP4 (SEQ ID NO. 10):
HRDSASEAIR KIPQCRTAI
```

EXAMPLE 2

PRRS Negative Herd (Nucleus Herd)

Herd Status: Animal tested derived from a boar nucleus herd. Boars will never be vaccinated against PRRSV and are closed meshed measured for the presence of PRRSV.

Animal Status: Animals are predicted to be negative for PRRSV directed antibodies.

Screening ELISA is negative as well as the discrimination ELISA.

Test interpretation: Animals are negative for PRRSV.

In the following the results are summarized in TABLES 5 and 6.

TABLE 5

| | Reference | Discriminatory ELISA | | | |
|---|---|---|---|---|---|
| | Test Idexx X3 | Type I (EU) | Type II (US) | Info Animal | Site Info |
| Neg | X | X | X | Boars | PRRSV negative |
| Pos | | | | | farm |
| Titre* | | <0.3 | <0.3 | | Nucleus herd |

TABLE 6

| Actual test results | | | | |
|---|---|---|---|---|
| | Information to animals | Discriminatory ELISA OD 450 nm-620 nm | | Reference Test |
| Sample No | and PRRS Status | Type I (EU) | Type II (US) | Idexx X3 ELISA |
| 12-2414 | BOARS | 0.026 | 0.068 | Neg |
| 12-2415 | PRRS | 0.060 | 0.032 | Neg |
| 12-2416 | negativer | 0.051 | 0.069 | Neg |
| 12-2417 | animals | 0.036 | 0.034 | Neg |
| 12-2418 | | 0.065 | 0.092 | Neg |

EXAMPLE 3

PRRS Negative Herd

Herd Status: Unknown. However, boars will never be vaccinated against PRRSV and are closed meshed measured for the presence of PRRSV.

Animal Status: Unknown

Screening ELISA is negative as well as the discrimination ELISA.

Test interpretation: Animals are negative for PRRSV.

In the following the results are summarized in TABLES 7 and 8.

TABLE 7

| | Reference | Discriminatory ELISA | | | |
|---|---|---|---|---|---|
| | Test Idexx X3 | Type I (EU) | Type II (US) | Info Animal | Site Info |
| Neg | X | X | X | Boars | PRRS |
| Pos | | | | | negative |
| Titre* | | <0.3 | <0.3 | | herd |

TABLE 8

| Actual test results | | | | |
|---|---|---|---|---|
| | Information to animals | Discriminatory ELISA OD 450 nm-620 nm | | Reference Test |
| Sample No | and PRRS Status | Type I (EU) | Type II (US) | Idexx X3 ELISA |
| 13-1107 | PRRS | 0.109 | 0.119 | Neg |
| 13-1108 | negative | 0.079 | 0.082 | Neg |
| 13-1109 | herd | 0.029 | 0.049 | Neg |
| 13-1110 | | 0.037 | 0.057 | Neg |
| 13-1111 | | 0.057 | 0.058 | Neg |

EXAMPLE 4

Herd with repeated PRRS Infection

Herd Status: Herd was positive tested in the past for the presence of PRRSV EU directed antibodies over years. Boars are continuously infected (repeated infections) with PRRSV.

Boars will never be vaccinated against PRRSV and are closed meshed measured for the presence of PRRSV.

Animal Status: Unknown

Screening ELISA is positive but not the discrimination ELISA.

Test interpretation: Animals losing their capability to establish a neutralising humoral immune response in a continuous, repeated PRRSV infection situation. However, these animals turned positive in a screening ELISA not measuring neutralising antibodies. These animals, even tested positive in the screening ELISA do not have anymore neutralising antibodies, indicating that a considerable proportion of antibodies are not present anymore.

→ Even aware that boars demonstrate only minor clinical signs of a PRRSV infection (e.g. fever) those animals may have a minor resistance capability against a heterologous PRRSV challenge (infection with PRRSV Type II in this assumed case, as animals are infected with EU type PRRSV).

In the following the results are summarized in TABLES 9 and 10.

TABLE 9

| | Reference | Discriminatory ELISA | | | |
|---|---|---|---|---|---|
| | Test Idexx X3 | Type I (EU) | Type II (US) | Info Animal | Site Info |
| Neg | | X | X | Boars | Farm with seroreactors, Continuous EU infected herd |
| Pos | X | | | | |
| Titre* | | <0.3 | <0.3 | | |

TABLE 10

| | Corresponding ELISA Results | | | |
|---|---|---|---|---|
| | Information to animals and PRRS Status | Discriminatory ELISA OD 450 nm-620 nm | | Reference Test |
| Sample No | | Type I (EU) | Type II (US) | Idexx X3 ELISA |
| 13-19 | Farm with | 0.082 | 0.131 | Pos! |
| 13-22 | seroreactors, | 0.070 | 0.061 | Pos! |
| 13-24 | Continuous | 0.076 | 0.100 | Pos! |
| 13-25 | EU infected | 0.043 | 0.072 | Pos! |
| 13-26 | herd | 0.038 | 0.087 | Pos! |

EXAMPLE 5

Repeated EU infected Boar Herd, freshly infected with US

Herd Status: Herd was positive tested in the past for the presence of PRRSV EU directed antibodies over years and turned recently positive for US PRRSV as proved by positive US PRRSV PCR results. Boars are continuously infected (repeated infections) with PRRSV. Boars will never be vaccinated against PRRSV and are closed meshed measured for the presence of PRRSV.

Animal Status: Unknown

Screening ELISA is positive and discrimination ELISA too.

Test interpretation: Animals losing their capability to establish a neutralising humoral immune response in a continuous, repeated PRRSV infection situation against EU PRRSV. However, these animals turned positive in the discrimination ELISA for PRRSV Type II (US). These animals tested positive in the screening ELISA.

Titre for US PRRSV are very high (>2 OD in average) indicating that a fresh infection with US PRRSV occurred in the herd. This test interpretation could be confirmed by PCR test results, demonstrating that the infection turned out to be in the viraemic phase.

Animals may have a minor resistance capability against a heterologous PRRSV challenge (infection with PRRSV Type II in this assumed case, as animals are infected with EU type PRRSV). Sows at gestation day 90, vaccinated with one of the MLVs but infected with a counter field PRRSV isolate would be the more profound sub species to prove the limited protection of the animals.

In the following the results are summarized in TABLES 11 and 12.

TABLE 11

| | Reference | Discriminatory ELISA | | | |
|---|---|---|---|---|---|
| | Test Idexx X3 | Type I (EU) | Type II (US) | Info Animal | Site Info |
| Neg | | X | X | Boar | Continuous EU infected herd (minimal 3 years), US positive since January 2013 |
| Pos | X | | | | |
| Titre* | | <0.3 | >1 | | |

TABLE 12

| | Corresponding ELISA Results | | | |
|---|---|---|---|---|
| | Information to animals and PRRS Status | Discriminatory ELISA OD 450 nm-620 nm | | Reference Test |
| Sample No | | Type I (EU) | Type II (US) | Idexx X3 ELISA |
| 12-2448 | Continuous | 0.140 | 0.381 | Pos! |
| 12-2449 | EU infected | 0.040 | 0.052 | Neg |
| 12-2450 | herd (minimal | 0.040 | 0.061 | Neg |
| 12-2451 | 3 years), US | 0.045 | 0.057 | Neg |
| 12-2452 | positive since | 0.044 | 0.051 | Neg |
| 12-2453 | January 2013 | 0.043 | 0.055 | Neg |
| 12-2454 | | 0.062 | 2.291 | Pos! |
| 12-2455 | | 0.095 | 2.055 | Pos! |
| 12-2456 | | 0.044 | 2.341 | Pos! |
| 12-2457 | | 0.177 | 2.478 | Pos! |

EXAMPLE 6

Maternal Interference or Building of First Neutralizing Antibodies

Herd Status: Piglets four weeks of age. Normally the age one week after vaccination against PRRSV. It is unknown if the sows have been vaccinated or not (based on the discrimination ELISA): It is predicted that the sows have been vaccinated with Porcilis PRRSV (EU PRRSV).

Animal Status: Unknown

Screening ELISA is positive and discrimination ELISA, too.

Test interpretation: Animals are actually too young to establish a humoral immune response against PRRSV. It is likely to assume that maternal interference (transfer of neutralising antibodies from sow to pig via suckling). It might be also possible that some mAB derived from the piglet immune system. Infection with wild PRRSV is unlikely due to the age of the piglets and the low titre measured in the discrimination ELISA.

In the following the results are summarized in TABLES 13 and 14.

TABLE 13

| Reference | Discriminatory ELISA | | | |
|---|---|---|---|---|
| Test Idexx X3 | Type I (EU) | Type II (US) | Info Animal | Site Info |
| Neg | | X | piglets of | unknown |
| Pos | X | X | 4 weeks, | |
| Titre* | <1 | <0.3 | fattening | |

TABLE 14

| | Corresponding ELISA Results | | | |
|---|---|---|---|---|
| | Information to animals | Discriminatory ELISA OD 450 nm-620 nm | | Reference Test |
| Sample No | and PRRS Status | Type I (EU) | Type II (US) | Idexx X3 ELISA |
| 13-2721 | unknown | 0.682 | 0.098 | Neg |
| 13-2722 | | 0.596 | 0.250 | Neg |
| 13-2724 | | 0.175 | 0.035 | Pos! |
| 13-2725 | | 0.923 | 0.206 | Pos! |
| 13-2727 | | 0.079 | 0.059 | Neg |

EXAMPLE 7

Ingelvac Vaccinated Herd (US PRRSV positive)

Herd Status: Piglets are ten weeks of age. Normally, this is the time six weeks after the vaccination against PRRSV normally took place. Pigs should demonstrate an intensive humoral immune response and high titre level are expected.

Animal Status: Unknown

Screening ELISA is positive and discrimination ELISA too.

Test interpretation: Animals are six weeks after vaccination. Based on the fact that only US PRRSV could be detected, with very high titres (average>1.0 OD), it is likely that these animals have been vaccinated with Ingelvac® PRRSV (US PRRSV).

In the following the results are summarized in TABLES 15 and 16.

TABLE 15

| Reference | Discriminatory ELISA | | | |
|---|---|---|---|---|
| Test Idexx X3 | Type I (EU) | Type II (US) | Info Animal | Site Info |
| Neg | X | | fattening, | unknown |
| Pos | X | X | 30 kg, ca. | |
| Titre* | <0.3 | >1 | 10 weeks of age | |

TABLE 16

| | Corresponding ELISA Results | | | |
|---|---|---|---|---|
| | Information to animals | Discriminatory ELISA OD 450 nm-620 nm | | Reference Test |
| Sample No | and PRRS Status | Type I (EU) | Type II (US) | Idexx X3 ELISA |
| 13-2738 | unknown, | 0.024 | 0.126 | Neg |
| 13-2743 | 30 kg | 0.051 | 0.498 | Pos! |
| 13-2744 | | 0.038 | 0.205 | Pos! |
| 13-2748 | | 0.031 | 0.756 | Pos! |
| 13-2749 | | 0.033 | 0.691 | Pos! |
| 13-2753 | | 0.055 | 2.894 | Pos! |
| 13-2754 | | 0.028 | 0.757 | Neg |
| 13-2755 | | 0.030 | 0.177 | Neg |
| 13-2756 | | 0.042 | 0.297 | Pos! |
| 13-2757 | | 0.085 | 0.405 | Neg |
| 13-2761 | | 0.033 | 2.703 | Pos! |
| 13-2762 | | 0.068 | 2.545 | Pos! |
| 13-2763 | | 0.023 | 0.395 | Pos! |
| 13-2764 | | 0.039 | 0.193 | Neg |
| 13-2765 | | 0.063 | 2.748 | Pos! |
| 13-2767 | | 0.047 | 2.379 | Neg |
| 13-2768 | | 0.113 | 2.788 | Pos! |
| 13-2772 | | 0.066 | 1.031 | Pos! |
| 13-2777 | | 0.107 | 2.769 | Pos! |
| 13-2778 | | 0.070 | 2.783 | Pos! |

EXAMPLE 8

Pig Herd Infected with Type I and II (EU and US) of PRRSV

Herd Status: Herd was positive tested in the past for the presence of PRRSV EU directed antibodies over years and turned recently positive for US PRRSV. Boars are continuously infected (repeated infections) with PRRSV. Boars will never be vaccinated against PRRSV and are closed meshed measured for the presence of PRRSV.

Animal Status: Unknown

Screening ELISA is positive and discrimination ELISA for EU and US, too.

Test interpretation: Animals tested positive in the past for EU PRRSV and very recently for US PRRSV. These animals tested positive in the screening ELISA. Titre for US PRRSV are very high (>1 OD in average) indicating that a fresh infection with US PRRSV occurred in the herd. Titre for EU PRRSV are low (<1 OD in average) indicating that an older infection with EU PRRSV occurred in the herd.

→ Old infection with EU PRRSV and fresh infection with US PRRSV

In the following the results are summarized in TABLES 17 and 18.

TABLE 17

| Reference | Discriminatory ELISA | | | |
|---|---|---|---|---|
| Test Idexx X3 | Type I (EU) | Type II (US) | Info Animal | Site Info |
| Neg | | | Boars | |
| Pos | X | X | X | |
| Titre* | <1 | >1 | | |

TABLE 18

Corresponding ELISA Results

| Sample No | Information to animals and PRRS Status | Discriminatory ELISA OD 450 nm-620 nm Type I (EU) | Discriminatory ELISA OD 450 nm-620 nm Type II (US) | Reference Test Idexx X3 ELISA |
|---|---|---|---|---|
| Boar 1 | Boars, | 0.037 | 0.044 | Neg |
| Boar 2 | | 0.031 | 0.029 | Neg |
| Boar 3 | | 0.052 | 0.063 | Neg |
| Boar 4 | | 0.039 | 0.038 | Neg |
| Boar 5 | | 0.115 | 2.408 | Pos! |
| Boar 6 | | 0.130 | 0.958 | Pos! |
| Boar 7 | | 0.030 | 0.038 | Neg |
| Boar 8 | | 0.035 | 0.063 | Pos! |
| Boar 9 | | 0.071 | 1.544 | Pos! |
| Boar 10 | | 0.267 | 2.584 | Pos! |
| Boar 11 | | 0.084 | 0.095 | Neg |
| Boar 12 | | 0.125 | 2.614 | Pos! |
| Boar 13 | | 0.035 | 0.423 | Pos! |
| Boar 14 | | 2.310 | 0.964 | Pos! |
| Boar 15 | | 0.440 | 1.539 | Pos! |
| Boar 16 | | 0.455 | 1.156 | Pos! |
| Boar 17 | | 0.035 | 0.044 | Pos! |
| Boar 18 | | 0.041 | 0.057 | Pos! |
| Boar 19 | | 0.029 | 0.031 | Pos! |
| Boar 20 | | 0.037 | 0.036 | Neg |
| Boar 21 | | 0.037 | 0.079 | Pos! |
| Boar 22 | | 0.092 | 0.257 | Pos! |
| Boar 23 | | 0.057 | 0.092 | Pos! |
| Boar 24 | | 0.103 | 1.192 | Pos! |
| Boar 25 | | 0.040 | 0.053 | Pos! |

EXAMPLE 9

Results of ELISA Assays Analyzing Serum Samples of Known PRRS Status

Discriminatory ELISA assays were performed on pig serum samples with known PRRS Status. 32 sera derived of vaccinated pigs (Type I (EU)), 20 sera derived of vaccinated pigs (Type II (US)) and 46 sera of PRRSV negative pigs were analyzed on EU specific peptides (left column) and US specific peptides (right column).

The results are depicted in TABLE 19.

The first number indicates amount of sample values over cutoff, right number indicates the total number of sample analyzed per cohort. In the 2 last rows the respective specificities and sensitivity is calculated.

TABLE 19

| PPRSV status of samples | Type of PRRSV strain | ELISA for PRRSV Type 1 (EU) Peptides GP3 and GP4 Number of corectly tested animals/ Number of tested animals | ELISA for PRRSV Type 2 (US) Peptides GP3 and GP4 Number of corectly tested animals/ Number of tested animals |
|---|---|---|---|
| Positive | PRRSV Type 1 (EU) | 20/32 | 7/32 |
| Positive | PRRSV Type 2 (US) | 0/46 | 19/20 |
| Negative | | 0/46 | 2/46 |
| Sensitivity | | 63% | 95% |
| Specificity | | 100% | 97% |

EXAMPLE 10

Diagnostic Composition (Kit)

A typical kit which can be used in the method according to the invention includes the components given in TABLE 20:

TABLE 20

| Component Name | Description |
|---|---|
| Component 1 Test Plate | High binding 96-well plate coated with PRRSV Type I/II specific peptides as follows: row 1, 3, 5, 7, 9, 11 coated with GP3/GP4 peptides specific for PRRSV Type I (EU) row 2, 4, 6, 8, 10 12 coated with GP3/GP4 peptides specific for PRRS Type II (US) |
| Component 2 Sample Diluent | Buffer used for diluting serum samples to be analyzed on the Test Plate (Component 1) |
| Component 3 Washing Fluid (20×) | Buffer used for rinsing unbound assay components after the sample incubation step and conjugate incubation step. |
| Component 4 Conjugate (30×) | Horse radish peroxidase labelled anti-pig antibody used for detection of antibodies bound to PRRSV Type I and Type II peptides. |
| Component 5 Conjugate Diluent | Buffer used for diluting the Conjugate (Component 4) during the conjugate incubation step. |
| Component 6 Positive Control EU | Serum of pig containing high antibodies titer specific for PRRSV Type I (EU) |
| Component 7 Positive Control US | Serum of pig containing high antibodies titer specific for PRRSV Type II (US) |
| Component 8 Weak Positive Control EU | Serum of pig containing low antibodies titer specific for PRRSV Type I (EU) |
| Component 9 Weak Positive Control US | Serum of pig containing low antibodies titer specific for PRRSV Type II (US) |
| Component 10 Negative Control | Serum of pig containing no antibody to the PRRS virus |
| Component 11 Substrate | Solution used as Enzymatic Substrate for HRP producing a color reaction |
| Component 12 Stop Solution | Solution used for stopping and stabilizing the color development |

EXAMPLE 11

Performance of Cocktails including further GP3 and GP 4 Peptides in Diagnostic Tests For this example for each case 4 Type I (EU) positive, 4 Type II (US) positive and 4 PRRS negative samples were analyzed by indirect ELISA (as described under example 1 in detail) using different cocktails of antigens. The results are discussed below referring to FIGS. 3-6.

a) Cocktail of Type I (EU)-Specific GP3 and GP4 Peptides

Figure 3:
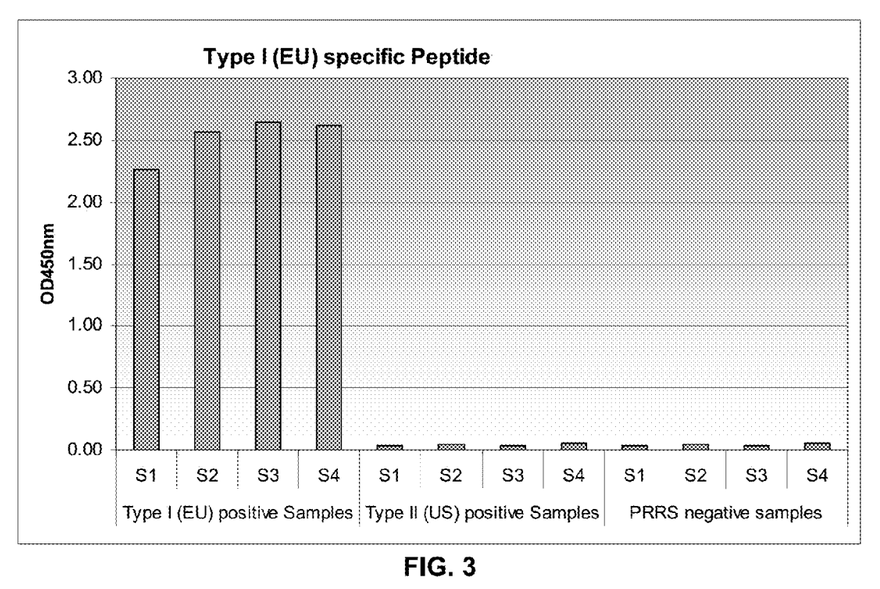

In this assay peptides according to SEQ ID NO. 5 (GP3) and SEQ ID NO. 7 (GP4) were used in combination. The results are shown in FIG. 3. One can see that all 4 Type I positive samples showed a clear signal with high intensity while the remaining further samples were identified as clearly negative.

b) Cocktail of Type I (EU)-Specific GP3 and GP4 Peptides

Figure 4:
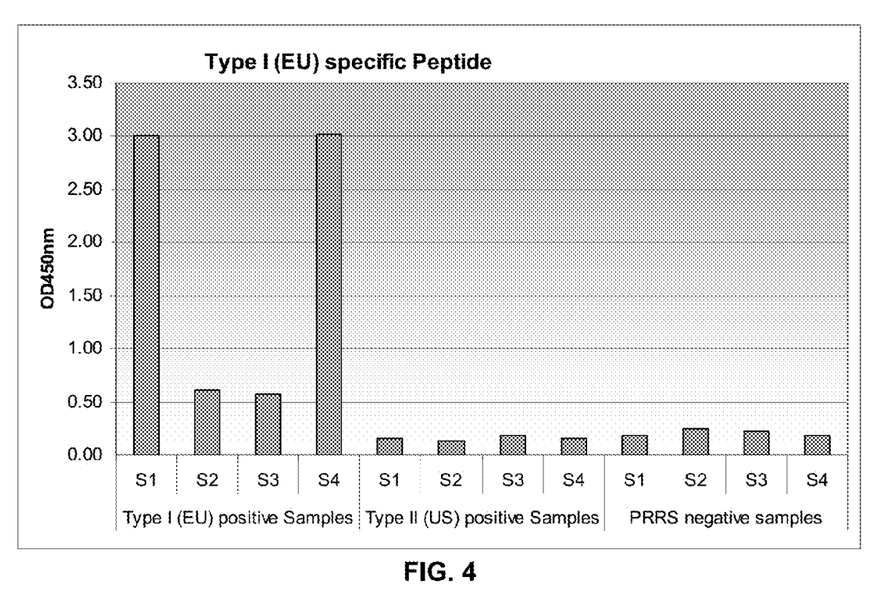

In this assay peptides according to SEQ ID NO. 6 (GP3) and SEQ ID NO. 2 (GP4) were used in combination. The results are shown in FIG. 4. One can see that all 4 Type I positive samples were identified positive with, however, signals of different intensity depending on the sample. The remaining Type II (US) positive and PRRS negative samples showed only weak signals and could still be clearly discriminated as negative.

c) Cocktail of Type II (US)-Specific GP3 and GP4 Peptides

Figure 5:
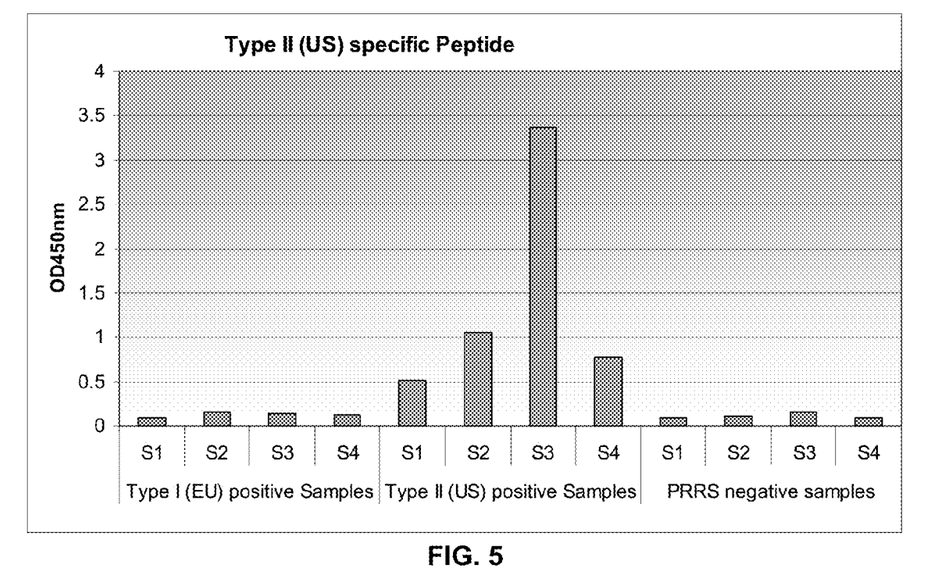

In this assay peptides according to SEQ ID NO. 8 (GP3) and SEQ ID NO. 10 (GP4) were used in combination. The results are shown in FIG. 5. One can see that all 4 Type II positive samples were identified positive with, however, signals of different intensity depending on the sample. The remaining Type I (EU) positive and PRRS negative samples showed only weak signals and could still be clearly discriminated as negative.

d) Cocktail of Type II (US)-Specific GP3 and GP4 Peptides

Figure 6:
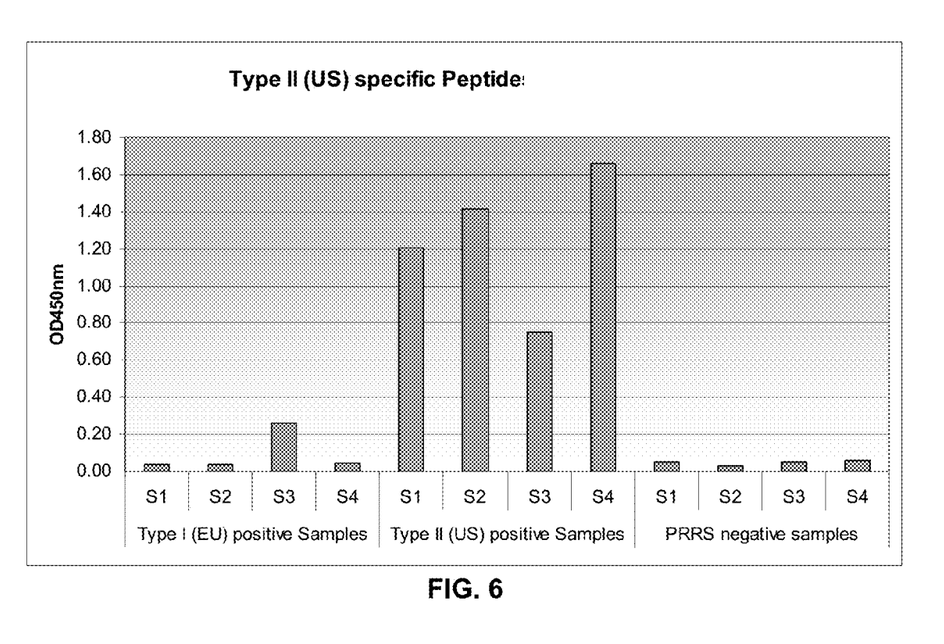

In this assay peptides according to SEQ ID NO. 9 (GP3) and SEQ ID NO. 10 (GP4) were used in combination. The results are shown in FIG. 6. One can see that all 4 Type II positive samples were identified positive with signals of higher intensity compared to example c. The remaining Type I (EU) positive and PRRS negative samples again showed only weak or no signals and could still be clearly discriminated as negative.

The invention claimed is:

1. A method for the detection and classification of PRRSV-infections in pigs comprising:
   a) incubation of a tissue sample taken from the pig with at least one antigen capable of binding to a neutralizing antibody against a PRRSV Type I-virus possibly present in the pig and/or with at least one antigen capable of binding to a neutralizing antibody against a PRRSV Type II-virus possibly present in the pig; and
   b) testing whether a binding of antibodies against the Type I-virus and/or the Type II-virus has taken place; and wherein:
   the PRRSV Type I peptide sequence containing a neutralizing epitope that is part of a GP3 protein of the PRRSV Type I serotype is SEQ ID NO. 1;
   or
   the PRRSV Type II peptide sequence containing a neutralizing epitope that is part of a GP3 protein of the PRRSV Type II serotype is SEQ ID NO. 3.

2. The method of claim 1, wherein the at least one antigen capable to bind a neutralizing antibody against the PRRSV Type I-virus is further selected from the group comprising the sequences of SEQ ID. NO: 5, SEQ ID. NO: 6, SEQ ID. NO: 2 and SEQ ID. NO: 7 and the at least one antigen capable to bind a neutralizing antibody against the PRRSV Type II-virus is further selected from the group comprising the sequences of SEQ ID. NO: 8, SEQ ID. NO: 9, SEQ ID. NO: 4, and SEQ ID. NO: 10.

3. The method of claim 2, wherein at least two antigens of the PRRSV Type II and at least two antigens PRRSV Type I sequences are used for the incubation.

4. The method of claim 2, wherein the peptide sequences are not longer than 50 amino acids.

5. The method of claim 1, further comprising measuring the titer of antibodies possibly present in the sample.

6. The method of claim 1 further comprising measuring non-neutralizing antibodies in the tissue sample.

7. A kit comprising:
   at least one antigen capable of binding to a neutralizing antibody against the PRRSV Type I-virus; and/or with at least one antigen capable of binding to a neutralizing antibody against the PRRSV Type II-virus; at least one or more buffers and solutions used in an ELISA-assay, wherein the at least one antigen capable of binding to a neutralizing antibody against the PRRSV Type I-virus contains a neutralizing epitope that is a peptide of a PRRSV GP3 protein and is SEQ ID NO. 1;
   or
   wherein the at least one antigen capable of binding to a neutralizing antibody against the PRRSV Type II-virus contains a neutralizing epitope that is a peptide of a PRRSV GP3 protein and is SEQ ID NO. 3.

* * * * *

SEQUENCE LISTING

```
<160> NUMBER OF SEQ ID NOS: 10

<210> SEQ ID NO 1
<211> LENGTH: 30
<212> TYPE: PRT
<213> ORGANISM: Artificial Sequence
<220> FEATURE:
<223> OTHER INFORMATION: Epitope sequence in GP3 of PRRSV Type I

<400> SEQUENCE: 1

Ile Cys Met Pro Cys Ser Thr Ser Gln Ala Ala Arg Gly Arg Leu Glu
1               5                   10                  15

Pro Gly Arg Ser Asn Met Cys Arg Lys Gly His Asp Arg Cys
            20                  25                  30

<210> SEQ ID NO 2
<211> LENGTH: 32
<212> TYPE: PRT
<213> ORGANISM: Artificial Sequence
<220> FEATURE:
<223> OTHER INFORMATION: Epitope sequence in GP4 of PRRSV Type I

<400> SEQUENCE: 2

Asp Ile Asn Cys Phe Arg Pro His Gly Val Ser Ala Ala Gln Glu Lys
1               5                   10                  15

Ile Ser Phe Gly Lys Ser Ser Gln Cys Arg Glu Ala Val Gly Thr Pro
            20                  25                  30

<210> SEQ ID NO 3
<211> LENGTH: 40
<212> TYPE: PRT
<213> ORGANISM: Artificial Sequence
<220> FEATURE:
<223> OTHER INFORMATION: Epitope sequence in GP3 of PRRSV Type II

<400> SEQUENCE: 3

Val Cys Pro Pro Cys Leu Thr Arg Gln Ala Ala Thr Glu Ile Tyr Glu
1               5                   10                  15

Pro Gly Arg Ser Leu Trp Cys Arg Ile Gly Tyr Asp Arg Cys Glu Glu
            20                  25                  30

Asp His Asp Glu Leu Gly Phe Met
        35                  40

<210> SEQ ID NO 4
<211> LENGTH: 28
<212> TYPE: PRT
<213> ORGANISM: Artificial Sequence
<220> FEATURE:
<223> OTHER INFORMATION: Epitope sequence in GP4 of PRRSV Type II

<400> SEQUENCE: 4

Asp Ile Ser Cys Leu Arg His Arg Asp Ser Ala Ser Glu Ala Ile Arg
1               5                   10                  15
```

```
Lys Ile Pro Gln Cys Arg Thr Ala Ile Gly Thr Pro
            20                  25

<210> SEQ ID NO 5
<211> LENGTH: 28
<212> TYPE: PRT
<213> ORGANISM: Artificial Sequence
<220> FEATURE:
<223> OTHER INFORMATION: Epitope sequence in GP3 of Prrsv Type I

<400> SEQUENCE: 5

Ser Thr Ser Gln Ala Ala Arg Gln Arg Leu Glu Pro Gly Arg Asn Met
1               5                   10                  15

Trp Cys Lys Ile Gly His Asp Arg Cys Glu Glu Arg
            20                  25

<210> SEQ ID NO 6
<211> LENGTH: 17
<212> TYPE: PRT
<213> ORGANISM: Artificial Sequence
<220> FEATURE:
<223> OTHER INFORMATION: Epitope sequence in GP3 of PRRSV Type I

<400> SEQUENCE: 6

Ser Thr Ser Gln Ala Ala Arg Gln Arg Leu Glu Pro Gly Arg Asn Met
1               5                   10                  15

Trp

<210> SEQ ID NO 7
<211> LENGTH: 19
<212> TYPE: PRT
<213> ORGANISM: Artificial Sequence
<220> FEATURE:
<223> OTHER INFORMATION: Epitope sequence in GP4 of PRRSV Type I

<400> SEQUENCE: 7

Phe Arg Pro His Gly Val Ser Ala Ala Gln Glu Lys Ile Ser Phe Gly
1               5                   10                  15

Lys Ser Ser

<210> SEQ ID NO 8
<211> LENGTH: 20
<212> TYPE: PRT
<213> ORGANISM: Artificial Sequence
<220> FEATURE:
<223> OTHER INFORMATION: Epitope sequence in GP3 of PRRSV Type II

<400> SEQUENCE: 8

Tyr Glu Pro Gly Arg Ser Leu Trp Cys Arg Ile Gly Tyr Asp Arg Cys
1               5                   10                  15

Gly Glu Asp Asp
            20

<210> SEQ ID NO 9
<211> LENGTH: 25
<212> TYPE: PRT
<213> ORGANISM: Artificial Sequence
<220> FEATURE:
<223> OTHER INFORMATION: Epitope sequence in GP3 of PRRSV Type II

<400> SEQUENCE: 9

Ile Tyr Glu Pro Gly Arg Ser Leu Trp Cys Arg Ile Gly Tyr Asp Arg
1               5                   10                  15

Cys Gly Glu Asp Asp His Asp Glu Leu
```

```
<210> SEQ ID NO 10
<211> LENGTH: 19
<212> TYPE: PRT
<213> ORGANISM: Artificial Sequence
<220> FEATURE:
<223> OTHER INFORMATION: Epitope sequence in GP4 of PRRSV Type II

<400> SEQUENCE: 10

His Arg Asp Ser Ala Ser Glu Ala Ile Arg Lys Ile Pro Gln Cys Arg
1               5                   10                  15

Thr Ala Ile
```